(12) United States Patent
Jo et al.

(10) Patent No.: US 9,976,940 B2
(45) Date of Patent: May 22, 2018

(54) COMPOSITION COMPRISING DNA BINDING PEPTIDE FOR DNA STAINING

(71) Applicant: INDUSTRY-UNIVERSITY COOPERATION FOUNDATION SOGANG UNIVERSITY, Seoul (KR)

(72) Inventors: Kyu Bong Jo, Goyang-si (KR); Seong Hyun Lee, Gunpo-si (KR); David C. Schwartz, Madison, WI (US)

(73) Assignee: INDUSTRY-UNIVERSITY COOPERATION FOUNDATION SOGANG UNIVERSITY, Seoul (KR)

( * ) Notice: Subject to any disclaimer, the term of this patent is extended or adjusted under 35 U.S.C. 154(b) by 15 days.

(21) Appl. No.: 15/100,145

(22) PCT Filed: Sep. 9, 2015

(86) PCT No.: PCT/KR2015/009499
§ 371 (c)(1),
(2) Date: May 27, 2016

(87) PCT Pub. No.: WO2016/159458
PCT Pub. Date: Oct. 6, 2016

(65) Prior Publication Data
US 2017/0122849 A1    May 4, 2017

(30) Foreign Application Priority Data
Mar. 27, 2015 (KR) .................. 10-2015-0043473

(51) Int. Cl.
*G01N 1/30* (2006.01)

(52) U.S. Cl.
CPC ......... *G01N 1/30* (2013.01); *G01N 2001/302* (2013.01)

(58) Field of Classification Search
CPC .......................................................... G01N 1/30
USPC ........................................... 435/6.1; 536/23.1
See application file for complete search history.

(56) References Cited

U.S. PATENT DOCUMENTS

| 5,436,134 A | 7/1995 | Haugland et al. .............. 435/34 |
| 6,348,317 B1 | 2/2002 | Thompson et al. .............. 435/6 |

OTHER PUBLICATIONS

Boutorine, A., et al. (2013) "Fluorescent probes for nucleic acid visualization in fixed and live cells." *Molecules*, 18(12):15357-15397. DOI: 10.3390/molecules181215357.

Dimicoli, J., et al. (1974) "Interactions of aromatic residues of proteins with nucleic acids. I. Proton magnetic resonance studies of the binding of tryptophan-containing peptides to poly(adenylic acid) and deoxyribonucleic acid." *Biochemistry*, 13(4):714-723. DOI: 10.1021/bi00701a013.

(Continued)

*Primary Examiner* — Jezia Riley
(74) *Attorney, Agent, or Firm* — Harness, Dickey & Pierce, P.L.C.

(57) ABSTRACT

The present invention relates to a composition for DNA staining, which can be safely used for researchers, can prevent DNA photocleavage, and can be applied to various fields. According to the present invention, when DNA is stained by using a fluorescent protein and a particular peptide bound to DNA, such a fluorescent protein-peptide is safe to researchers, suppresses DNA photocleavage, and allows reversible staining, thereby enabling efficient DNA staining. Therefore, the composition for DNA staining of the present invention can be variously used in DNA-related research.

10 Claims, 8 Drawing Sheets

(56) References Cited

OTHER PUBLICATIONS

Fedoreyeva, L., et al. (2011) "Penetration of short fluorescence-labeled peptides into the nucleus in HeLa cells and in vitro specific interaction of the peptides with deoxyribooligonucleotides and DNA." *Biochemistry (Moscow)*, 76(11):1210-1219.

Glazer, A., et al. (1992) "Stable dye-DNA intercalation complexes as reagents for high sensitivity fluorescence detection." *Nature*, 359:859-861.

Helene, C., et al. (1972) "Interaction of oligopeptides containing aromatic amino acids with nucleic acids. Fluorescence and proton magnetic resonance studies ." *FEBS Letters* 26(1):6-10. DOI: 10.1016/0014-5793(72)80529-5.

Japaridze, A., et al. (2015) "Influence of dna binding dyes on bare dna structure studied with atomic force microscopy." *Macromolecules*, 48(6):1860-1865. DOI: 10.1021/ma502537g.

Lee, (2015) "DNA binding fluorescent proteins for the direct visualization of large DNA molecules." *Nucleic Acids Research*, 44(1):1-9. DOI: 10.1093/nar/gkv834.

Kim, Y. et al. (2011) "Neutravidin coated surfaces for single DNA molecule analysis." *Chem. Commun.*, 47:6248-6250.

Mascotti, D., et al. (1992) "Thermodynamics of single-stranded RNA binding to oligolysines containing tryptophan." *Biochemistry*, 31(37):8932-8946. DOI: 10.1021/bi00152a033.

Mascotti, D., et al. (1993) "Thermodynamics of single-stranded RNA and DNA interactions with oligolysines containing tryptophan. Effects of base composition." *Biochemistry*, 32(40):10568-10579. DOI: 10.1021/bi00091a006.

Minoshima, M., et al. (2014) "Development of a fluorogenic probe based on a DNA staining dye for continuous monitoring of the histone deacetylase reaction." *Anal. Chem.*, 86(15):7925-7930. DOI: 10.1021/ac501881s.

Montenay-Garestier, T., et al. (1968) "Molecular interactions between tryptophan and nucleic acid components in frozen aqueous solutions." *Nature*, 217:844-845. DOI: 10.1038/217844a0.

Tycon, M., et al. (2012) "Quantification of dye-mediated photodamage during single-molecule DNA imaging." *Analytical Biochemistry*, 426:13-21. DOI: 10.1016/j.ab.2012.03.021. Epub Apr. 4, 2012.

International Search Report (ISR) in PCT/KR2015/009499, dated Nov. 10, 2015.

DNA staining eGFP

YOYO-1 pH 8.0, 0 sec pH 11.0, 150 sec pH 8.0, 300 sec

COMPOSITION COMPRISING DNA BINDING PEPTIDE FOR DNA STAINING

CROSS-REFERENCE TO RELATED APPLICATIONS

This application is a national phase application of PCT Application No. PCT/KR2015/009499, filed on Sep. 9, 2015, which claims priority and the benefit of Korean Patent Application No. 10-2015-0043473, filed Mar. 27, 2015, in the Korean Intellectual Property Office. The entire disclosures of the applications identified in this paragraph are incorporated herein by references.

FIELD

The present invention was made with the support of the Ministry of Science, ICT, and Future Planning of the Republic of Korea, under Project No. 2014R1A2A2A04003870, which was conducted under the research project entitled "Middle-Grade Researcher Supporting Project" within the project named "Super-sensitive DNA Damage Detection Biosensor Using Single DNA Molecules" by the Industry-Academic Cooperation Foundation, SOGANG University under the management of the National Research Foundation of Korea, from 1 May 2014 to 30 Apr. 2017, and No. 2016R1A6A1A03012845, which was conducted under the research project entitled "Middle-Grade Researcher Supporting Project" within the project named "Development of Nanobiochip Platform to Analyze Drug Evaluation in Brain Disease" by the Industry-Academic Cooperation Foundation, SOGANG University under the management of the National Research Foundation of Korea, from 1 May 2016 to 31 Dec. 2024.

The present invention relates to a composition comprising DNA binding peptide for DNA staining.

BACKGROUND

Approaches using genetically engineered fluorescent protein (FP) have revolutionized cell and molecular biology. Fluorescent proteins have worked as reporters within a living cell by tagging protein, allowing for the understanding of protein functions by visualizing molecular motions and localizations in real time. Meanwhile, with respect to DNA molecules, there are studies on the migration of particular proteins on the DNA molecules using fluorescent proteins, but there have been no reported study results about the staining of DNA molecules per se using fluorescent proteins in order to visualize DNA molecules.

DNA molecules are usually stained by fluorescent organic dyes. For example, intercalating dyes of ethidium bromide (EtBr) are widely used for staining DNA after gel electrophoresis. Under a fluorescent microscope, large DNA molecules are often visualized by a bis-intercalating dye of oxazole yellow homodimer (YOYO) (1). Within a living cell, DNA is often stained by membrane permeable dyes such as SYTO (2).

Such intercalating dyes have advantages of staining DNA through a simple procedure and showing high signal-to-noise ratios and low dissociation constants (Kd=12.2 μM for EtBr, Kd=12.1 nM for YOYO-1) (1, 2). However, these organic dyes have the following disadvantages due to intrinsic characteristics thereof. Since the organic dyes are ex vivo induction materials, they act as a potential mutagen, and thus the attention of researchers is required. When the organic dyes are irradiated with a laser for fluorescence, a radical intermediate is formed, causing the photocleavage of DNA phosphoric acid backbone, and thus samples cannot be further used in tests (3-7). In order to solve these problems, many researchers are endeavoring to develop safe and convenient DNA staining materials.

Numerous journal articles and patent documents are referred to herein over the entire specification and indicated as referred to. The disclosure of the cited journal articles and the patent documents are incorporated herein in their entirety by reference to further elucidate the level of the technologies to which the present invention belongs and the details of the present invention.

SUMMARY

Technical Problem

The present inventors researched and endeavored to develop a material for DNA staining that can be safely used for researches, can prevent DNA photocleavage, and can be applied to various fields. As a result, the present inventors verified that, when a fluorescent protein is linked to a particular peptide binding to DNA, such a fluorescent protein-peptide is safe to researchers, suppresses DNA photocleavage, and efficiently stains DNA.

An aspect of the present invention is to provide a novel composition for DNA staining containing a DNA-binding peptide.

The present invention have other features and advantages which will be apparent from or are set forth in more detail in the accompanying drawings, which are incorporated herein, and the following Detailed Description of the Invention, which together serve to explain certain principles of the present invention.

Technical Solution

In accordance with an aspect of the present invention, there is provided a composition for DNA staining, the composition being represented by General Formula 1, 2, or 3:

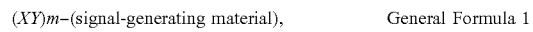

(XY)m–(signal-generating material),          General Formula 1

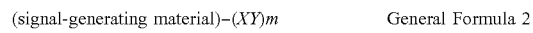

(signal-generating material)–(XY)m          General Formula 2 wherein in general formulas 1 and 2, X is Lys or Arg; Y is Trp or Tyr; the order of X and Y may be inverted; and m is an integer of 1 to 10; and

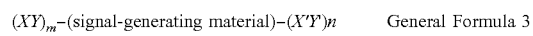

(XY)m–(signal-generating material)–(X'Y')n          General Formula 3 wherein in the above general formula, X is Lys or Arg; Y is Trp or Tyr; the order of X and Y may be inverted; X' is Lys or Arg; Y' is Trp or Tyr; the order of X' and Y' may be inverted; and m and n each are an integer of 1 to 10.

The composition for DNA staining of the present invention contains a DNA-binding peptide and a signal-generating material.

The DNA-binding peptide is composed of repetitive connections of a positively charged amino acid and an amino acid having an aromatic ring. (XY)m.

X is a positively charged amino acid (for example, lysine or arginine); Y is an amino acid having an aromatic ring (for example, tryptophan or tyrosine); and the order of X and Y may be inverted. Preferably, as a result of staining DNA with a combination of X and tryptophan, DNA can be clearly visualized. m is an integer of 1 to 10. The lower the m value, the lower the binding affinity, but there is less noise in the background. While, the higher the m value, the higher the binding affinity, but there is increased noise in the background. According to a certain embodiment of the present invention, DNA can be clearly visualized without background noise if m is 2.

The DNA-binding peptide may be located at the N-terminus, the C-terminus, or both of the N-terminus and the C-terminus of the signal protein. When the DNA-binding peptide is located at both of the N-terminus and C-terminus, the binding specificity is increased and thus the background noise may be reduced. According to a specific embodiment of the present invention, when the DNA-binding peptide is located at both of the N-terminus and the C-terminus and m is 2, DNA can be clearly visualized without background noise.

The signal-generating material of the present invention is a material that can generate a detectable signal, and examples thereof may include a fluorescent protein, a luminescent protein, a color reaction-catalyzing enzyme (e.g., alkaline phosphatase, peroxidase, β-galactosidase, or ρ-glucosidase), a chemical material (e.g., biotin), a fluorescent material (e.g., fluorescein, TAMRA, Cy5, Cy3, HEX, TET, Dabsyl, or FAM), a luminescent material, a chemiluminescent material, and the like, but are not limited thereto. Preferably, the signal-generating material is a fluorescent protein or a luminescent protein. According to a specific embodiment of the present invention, DNA was visualized using a green fluorescent protein and a red fluorescent protein.

In the present invention, the DNA-binding peptide may be linked to the signal-generating material via a linker. Various kinds of linkers that can link the DNA binding peptide and the signal-generating material may be used depending on the kind of signal-generating material. Specifically, a peptide linker including at least two amino acids selected from the group consisting of glycine, serine, lysine, and alanine may be used, and more specifically, a peptide linker including lysine and alanine may be used. According to a specific embodiment of the present invention, DNA was successfully visualized using a KKA linker including lysine and alanine.

According to another aspect of the present invention, there is provided a method for staining DNA, the method including a step of applying the composition of the present invention to a sample containing DNA.

The sample, to which the composition of the present invention is applied, includes biological samples (e.g., cells, tissues, and body fluids), and examples of the biological sample are viruses, bacteria, tissues, cells, bloods (including whole blood, plasma, and serum), a solution containing isolated DNA, lymph, bone marrow fluid, saliva, milk, urine, faces, ocular fluid, semen, brain extract, spinal fluid, joint fluid, thymus fluid, ascitic fluid, and amniotic fluid.

The method, by which the composition of the present invention is applied to sample, includes: a method for bringing the composition into direct contact with a sample; and a method for inducing a vector capable of expressing the composition into bacteria or cells. According to a specific embodiment of the present invention, the vector capable of expressing the composition of the present invention is introduced into *E. coli* to enable the expression of the composition in *E. coli*, thereby successfully visualizing *E. coli* DNA.

Advantageous Effects

Features and advantages of the present invention are summarized as follows:

(a) The present invention provides a composition for DNA staining containing a DNA-binding peptide.

(b) The composition for DNA staining of the present invention is safe to the human body, suppresses DNA photocleavage, and allows reversible staining, and can thus be applied to various research fields.

DETAILED DESCRIPTION

Figure 1:
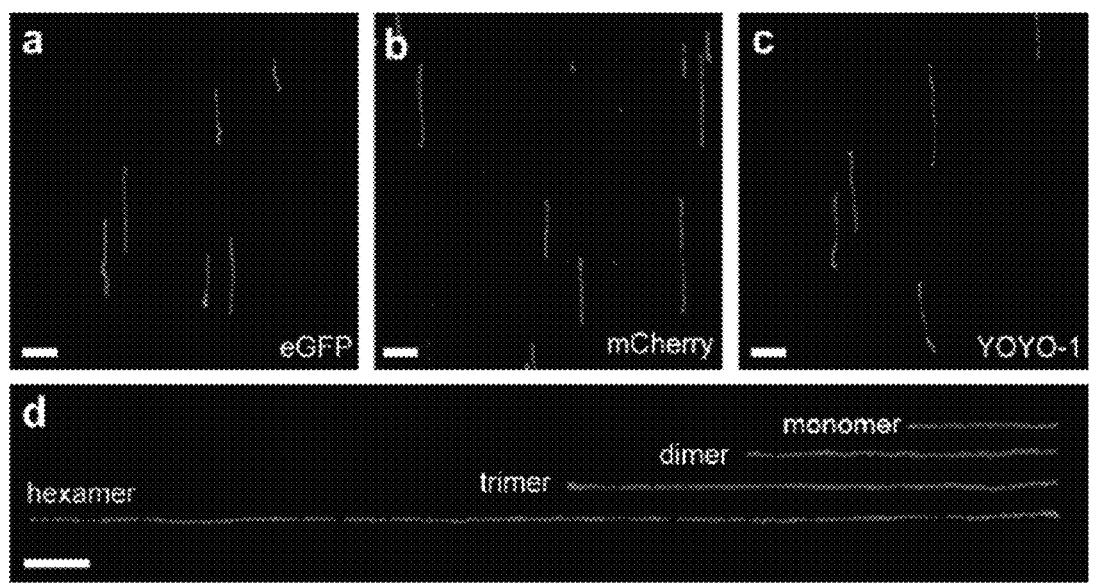
FIG. 1 illustrates fluorescence microscopic images showing single DNA molecules stained with fluorescent proteins to which peptides are linked. λ DNA (48.5 kb) stained with (a) DNA staining eGFP, (b) mCherry, which is a red fluorescent protein, and (c) YOYO-1, which is an organic dye, and (d) λ DNA concatemers stained by DNA staining eGFP. Scale bars are 5 μm.

Hereinafter, the present invention will be described in greater details with reference to the accompanying examples. However, these examples disclosed herein are only for illustrative purposes of the present invention, and it shall be obvious to a skilled person in the art that they should not be construed as limiting the scope of the present invention.

Materials and Methods
Reagents

All of the DNA primers and oligonucleotides were purchased from Bioneer (Daejeon, Korea). All enzymes were purchased from New England Biolabs (Ipswich, Mass.). λ DNA (48.5 kb) was purchased from Bioneer (Daejeon, Korea) and T4 GT7 DNA (165,644 bp) was purchased from Nippon Gene (Tokyo, Japan). *E. coli* strain BL21 (DE3) was purchased from Yeastern (Taipei, Taiwan). Biotin-labeled bovine serum albumin (BSA) was from Sigma (St. Louise, Mich.), neutravidin was from Pierce (Rockford, Ill.), and BSA was from New England Biolabs (Ipswich, Mass.). Epoxy was from Devcon (Riviera Beach, Fla.). N-trimethoxymethylsilylpropyl-N,N,N-trimethylammonium chloride in 50% Methanol was purchased from Gelest (Morrisville, Pa.). Ni-NTA agarose resin and disposable column (empty gravity column) was purchased from Qiagen (Venlo, Netherlands). Non-SDS TBE-PAG was purchased from Komabiotech (Seoul, Korea). Other chemicals were from Sigma.

Protein Construction

The plasmid pET-15b (Novagen, Germany) was used for the transformation and expression of DNA-staining eGFP (pEGFP-N1, Clontech, USA). For tagging DNA binding parts to each terminals of eGFP, forward primer (5'-ATG TTG CAT ATG AAA TGG AAA TGG AAA AAA GCG ATG CGT) and reverse primer (5'-ATG TTG GGA TCC TTA TTT CCA TTT CCA TTT TTT CGC CTT GTA CAG CTC GTC CAT GCC-3') were used in the PCR process. Restriction sites included the NdeI and BamHI sites. Using a typical subcloning procedure, DNA-staining FPs in pET-15b vector was constructed and transformed into the E. coli BL21 (DE3) strains for the purpose of protein expression. A single colony of the transformed cells was inoculated in a fresh LB media containing ampicillin. After inoculation of transformed cell, they were grown up to an optical density of ~0.8 without IPTG. IPTG was used for induction and overexpression, and the transformed cells were inoculated in the media with a final concentration of 1 mM for IPTG. Following this, the cells for overexpression were kept on a shaker at a temperature less than RT for 24 hr, and cells for direct observations were collected at the desired time, which come an optical density over 2.0. Cells for the protein purification were harvested by centrifugation at 12,000×g, for 10 min (following centrifugations were performed under similar conditions), and the residual media was washed using the cell lysis buffer (50 mM $Na_2HPO_4$, 300 mM NaCl, 10 mM Imidazole, pH 8.0). Cells were lysed by ultrasonication for 1 hr and cell debris was separated by centrifugation. Ni-NTA agarose resin was added to the supernatants, and the mixture of the resin and cell proteins were kept on a shaker at 4° C. for 6 hr. The resin containing the bound protein was packed in an empty column for gravity chromatography, was further rinsed several times with protein wash buffer (50 mM $Na_2HPO_4$, 300 mM NaCl, 20 mM Imidazole, pH 8.0), and the bound proteins were finally eluted using the protein elution buffer (50 mM $Na_2HPO_4$, 300 mM NaCl, 250 mM Imidazole, pH 8.0). Following this, no further protein purification procedures were performed. Protein concentrations were 10 mg/ml for eGFP, and 6 mg/ml for mCherry. All proteins were diluted to adequate concentration using 50% w/w glycerol/1×TE buffer (Tris 10 mM, EDTA 1 mM).

Preparation of Cover Slips and Devices Necessary for Tests

1. Preparation of Cover Slips and Modified Surface

Cover slips necessary for a DNA staining test using fluorescent proteins for DNA staining were prepared through the following procedure. The glass coverslips were stacked in the Teflon rack, and soaked in piranha etching solution (30:70 v/v $H_2O_2/H_2SO_4$) for 2 hr. After thorough rinsing of the coverslips with deionized water for several times, acid cleaned surfaced was used for protein coating. To adhere the positive charges on the surface, 200 µl of N-trimethoxymethylsilylpropyl-N,N,N-trimethylammonium chloride in 50% methanol was added to 200 ml of deionized water. The glass coverslips were incubated in this solution for 12 hr, 65° C. These derivatized glass surfaces were used within 2 weeks of their preparation.

2. Preparation of Microchannels and Nanoslits

A silicon wafer for 4 µm-high microchannels and 450 nm-high nanoslits was fabricated using lithography. SU-8 2005 photoresist (Microchem, Newton, Mass.) was spin-coated onto the silicon wafer, followed by baking and exposure to 350 nm UV, thereby forming patterns. After, the patterned wafer was baked again and developed using a SU-8 developer (Microchem). The thus fabricated microchannels were used without further treatment (soft lithography).

450 nm-high hard lithographic patterns (etching patterns) were used for the fabrication of nanoslits, and 4 µm-high microchannel layers were placed thereon in the same manner as above. Thereafter, polydimethylsiloxane (PDMS) Sylgard 184 Elastomer (Dow corning, MI, USA) was hardened on various patterns for use.

3. Flow Cell

The flow cell was made in order to stretch the DNA molecule using fluid flow after one end of the DNA molecule is fixed. First, a cover slip was placed on the glass slide with a spacing of 100 µm between the two, using a double-sided tape. The inlet and outlet holes were drilled on this microscope glass slide using a diamond-coated bit. All glasses were washed with piranha solution. A yellow pipette tip was installed in the inlet port and a tubing line was connected to the outlet port with an epoxy bonding that was cured at RT for 5 min. Further, the cover slip was fixed on the glass slide using a double-sided 3M tape. The dimensions of the flow cell were 3×17×0.1 mm (L×W×H) and the total volume of the flow cell was 5.1 µL. A syringe pump, NE-1000 (New Era Pump Systems Inc., Wantagh, N.Y.), was used to control the buffer delivery into the flow cell with a flow rate of 0.150 mL/min that corresponded to 8.3 mm/sec.

4. Preparation of Surface Modified with Proteins

The glass surface of the microfluidic flow channel was coated with diluted biotin-BSA (1 mg/mL, 10 mM Tris, 50 mM NaCl, pH 8.0) to be modified with proteins. After five minutes of BSA adsorption, neutravidin solution (0.25 mg/mL 10 mM Tris, 50 mM NaCl, pH 8.0) was loaded into the BSA-coated flow cell. The setup was kept at RT for 5 min. After five minutes of neutravidin adsorption, the flow cell was further coated with a hundred times diluted BSA stock solution (in TE buffer). The flow cell setup was again kept at RT for 5 min.

Staining of Single DNA Molecules Using Fluorescent Proteins for DNA Staining

The proteins purified by the above method were diluted to 10 µg/ml, and target DNA molecules to be stained wee diluted (0.2 ng/µl, 1×TE, pH 8). The diluted DNA molecules were then mixed at 1:1 (v/v) with the diluted fluorescent proteins for DNA staining, followed by reaction in tube at room temperature for 5 minutes. The fluorescent protein for DNA staining-DNA sample after the completion of the reaction was electrostatically attached to the bottom surface and stretched while being allowed to flow through the microchannels (height 4 µm) fabricated by the method, followed by fluorescent microscopic observation.

Fluorescence Microscope and DNA Visualization

The microscopy system consisted of an inverted microscope (Olympus IX70, Tokyo, Japan) equipped with 63× and 100× Olympus UPlanSApo oil immersion objectives, illuminated using a solid-state laser (LBX488 and SLIM 532, Oxxius, Lannion, France). The laser light was focused on the multimode optical fiber (BFH-22-550, Thorlabs, Newton, N.J.) and passed through a 488 nm and 532 nm holographic notch filter (Semrock, Rochester, N.Y.), which was installed to prevent laser lights from reaching the EMCCD camera. Fluorescence images were captured by an electron-multiplying charge-coupled device digital camera (QimagingRolera EM-C2, Surrey, BC, Canada) and stored as 16 bit TIFF format generated by the softwareImage Pro Plus (Media Cybernetics, Rockville, Md.). For image processing and length measurements, ImageJ was utilized with Java plug-ins developed in our lab.

Analyzing Dissociation Constants of Fluorescence Proteins for DNA Staining: EMSA (Electrophoretic Mobility Shift Assay)

A 52-mer random sequence oligonucleotide (5'-CTA CTA GCA CAA TCG ACT GTA CGG ACC GAT CGA GTC ACT AGC AGT CTA GCA A-3') and its complementary sequence oligonucleotide are hybridized into double strands DNA. The same molar concentrations of two oligonucleotides in a microcentrifuge tube were soaked in boiled water, followed by cooling down to the room temperature. Hybridized double strands DNA oligo was diluted to 0.5 ng/μL (~31.4 nM) using 1×TE buffer. DNA staining FPs was diluted with 50% v/v glycerol/1×TE, and corresponding molar concentrations are 74 nM, 740 nM, 1.48 μM, 3.7 μM, 7.4 μM, 14.8 μM, 37 μM, 74 μM, and 148 μM, respectively. The diluted proteins, DNA oligomer, and 50% v/v glycerol/1×TE buffer to adjust total reaction volume (10 μl) were added to each sample tube. Each sample was loaded into 0.5×TBE 4%-20% polyacrylamide precast gel (TBE-PAG). After running 75 min at 151 V constant, the gel was stained with EtBr for 5 min, and was destainedexcess EtBr in deionized water for several minutes. Images of retarded DNA were captured with CCD camera (WGD-20, Daihan Scientific Co., Korea) on UV transilluminator (WUV-M20, Daihan Scientific Co., Korea). Fraction bounds of each lane were represented as intensity profiles of bound proteins/free DNA, and analyzed with ImageJ Gel Analyze. Apparent dissociation constants of protein concentrations were calculated as Kd=(1−f)/f× [Protein] total (f: fraction bound).

Analysis on DNA Sequence Specificity of Fluorescent Proteins for DNA Staining

For the analysis of DNA sequence specificity of fluorescent proteins for DNA staining, MALDI-TOF mass spectroscopy was conducted. After a binding reaction of DNA oligonucleotides and peptides, MALDI-TOF mass spectroscopy was conducted. All oligonucleotides used in the test were diluted to 100 μM using TE buffer, and the peptides were diluted to 100 μM using tertiary purified water for use. The peptide binding reaction was conducted in the total reaction volume of 20 μL. 10 μL of oligonucleotides and 10 μL of peptides were added to each sample tube to adjust to a total reaction volume of 20 μL, followed by reaction at room temperature for 30 minutes. The sample after the completion of the reaction was mixed at 1:1 (v/v) with a matrix solution (130 mM 2,5-dihydroxybenzoic acid (DHB)), and placed on the Bruker MTP 384 polished steel MALDI sample support target plate. The sample crystallized at room temperature and the matrix were analyzed in a linear positive ion mode using Bruker Autoflex™ Speed (Bruker Daltonics Inc., Billerica, Mass.). Mass spectrum can be obtained by the sum of 500 laser shots at 1000 Hz.

In Vivo DNA Staining Using Fluorescent Proteins for DNA Staining

In order to directly stain DNA in vivo using fluorescent proteins for DNA staining, *E. coli* BL21 (DE3) strains transformed with an expression vector of the fluorescent proteins for DNA staining were used in the preparation procedure of the fluorescent proteins for DNA staining. The cells were grown until OD 600 nm exceeds 2.0, and then IPTG was added to a final concentration of 1 mM. The cells, after sufficient time of IPTG addition, were taken at 1 μl, placed on a cover slip with 22×22 mm, followed by microscope observation without other special treatment.

Analysis on Photocleavage by Fluorescent Proteins for DNA Staining

In order to analyze whether the photocleavage occurs by fluorescent proteins for DNA staining, the following cover slip was prepared. A cover slip was placed on a fixing plate of acryl resin with a square hole (20×20 mm), and then the edges of the cover slip excluding one side of the glass surface was coated with wax, thereby exposing the one side of the glass surface to be tested and preventing the flowing out of a solution (50 mM EDTA) for electrical conduction. Further, in order to make electrodes for DNA migration, a copper wire was attached on the acryl fixing plate in the direction of a diagonal line of the square hole. The 450 nm-high PDMS nanoslits fabricated by the above method were placed on the prepared cover slip, and then a mixture solution of eGFP protein for DNA staining and T4GT7 DNA was allowed to flow. Then, about 400 μl of 50 mM EDTA solution was put around the nanoslits to enable electrical conduction through the copper wire. In order to allow DNA molecules to be placed in the nanoslits formed between the microchannels through electrical attraction, a device with a switch capable of controlling the direction of both electrodes under a voltage of 30 V was used. After DNA molecules were placed in the nanoslits, it was observed whether photocleavage occurs through the irradiation of laser.

Reversible Staining

Figure 2:
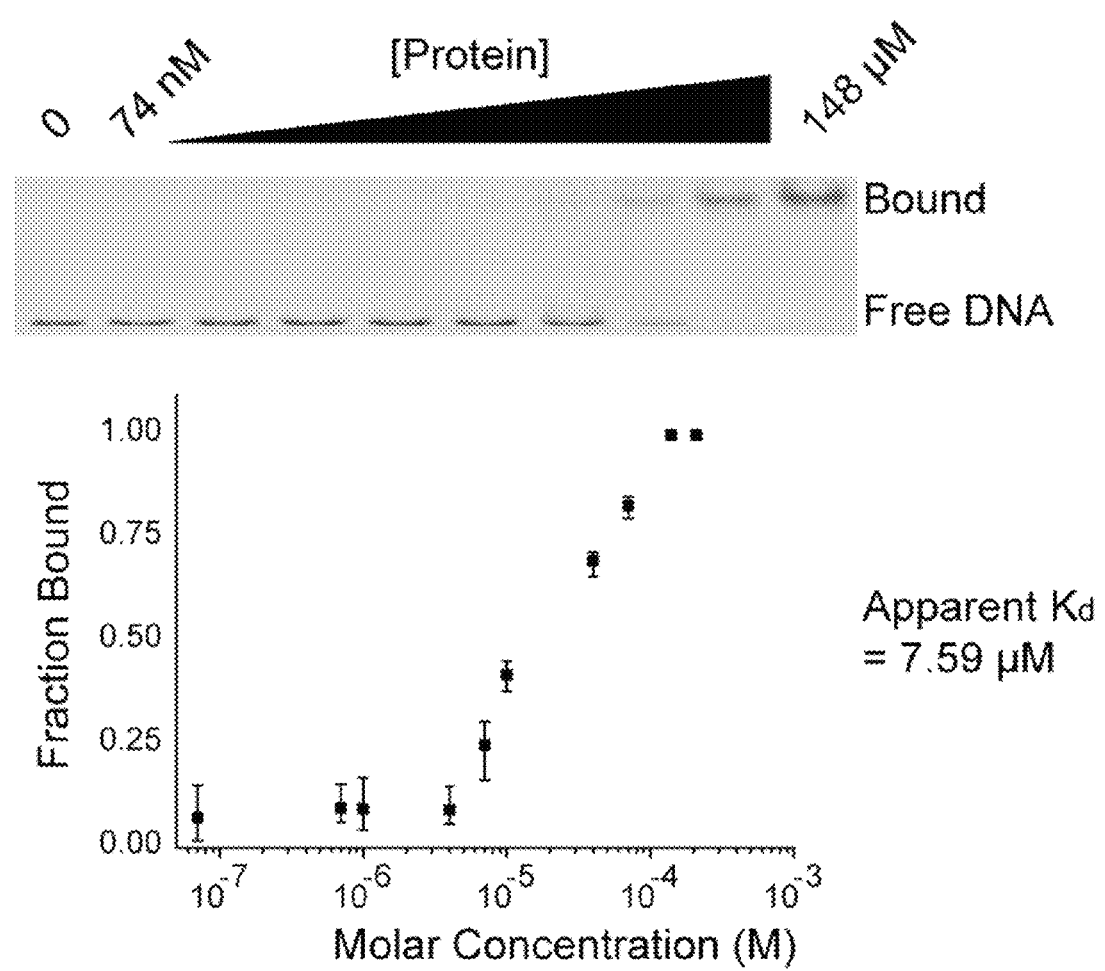
FIG. 2 illustrates a dissociation constant of DNA-binding fluorescent proteins analyzed through electrophoretic mobility shift assay (EMSA). The electrophoretic gel image shows that DNA staining fluorescent protein is bound to DNA.

After the preparation of neutravidin-coated surfaces in FIG. 2, 220 pmoles of λ DNA overhang oligo (5'-pGGGCG-GCGACCT-TEG-biotin-3') were loaded into the flow cell, and kept at RT for 5 min. The λ DNA, T4 DNA ligase, and the reaction buffer were added, and kept at RT for 30 min. The diluted DNA-staining eGFP flowed into the channels resulting in the visualization of the tethered DNA. For the purpose of de-staining of the attached eGFP, 50 μl of TE buffer (adjusted to pH 11.0) was loaded in the flow cell. The residual buffer was immediately washed 200 μl of TE buffer (pH 8.0) and then diluted proteins were loaded. The visualization of the stained DNA molecules was done under a continuous flow of the TE buffer (pH 8.0) with a flow rate maintained at 20 μL/min.

Analysis on Influence on DNA Contour Lengths by Fluorescent Proteins for DNA Staining Still images of DNA molecules used in the reversible staining were photographed, and the DNA contour lengths were measured using ImageJ programs. A total of 295 single DNA molecules were analyzed.

Results

Staining of Single DNA Molecule Using Fluorescent Proteins for DNA Staining

Single DNA molecules were stained using fluorescent proteins for DNA staining. As the DNA-binding peptide therefor, KWKKA obtained by linking a linker (lysine-alanine, KA) to a combination of lysine and tryptophan was used, and the linker is linked to the N-terminus of fluorescent proteins to prepare fluorescent proteins for DNA staining. As a result of confirmation through electrophoretic mobility shift assay, the KWKKA-linked fluorescent proteins bound to DNA, but had binding strength that was insufficient to confirm staining or no staining through a fluorescent microscope. Therefore, the repetition number of amino acids was increased in order to improve binding affinity. Such an idea is obtained from papers (7, 8) showing that the binding strength of peptides was measured with an increasing number of tryptophan residues while five lysine residues are fixed, for example, KKKKK, KWKKKK, and KWKKKWK. The phenomenon was used in which the increasing number of tryptophan residues leads to a high binding constant. Based on this idea, (KW)$_5$KKA-eGFP, as a fluorescent protein having higher binding affinity, was prepared. As a result of DNA stained with (KW)$_5$KKA-eGFP, the large single DNA molecules were successfully visualized on a fluorescent microscope, but light points, such as noise, (that is, many materials that are assumed as protein aggregates) were shown on the screen. In order to solve the problems, fluorescent proteins having a structure of (KW)$_5$KKA-eGFP-AKK(WK)$_5$ were prepared by further linking the (KW)$_5$KKA peptides to the C-terminus of eGFP. This is for minimizing undesired protein-protein interactions by exhibiting more positive charges in one protein. However, in cases where fluorescent proteins have a structure of (KW)$_5$KKA-eGFP-AKK(WK)$_5$ are used, the light points, such as noise, were not shown, but DNA molecules were not visualized. The reason was assumed to be that excessive positive charges generated due to the stretching of peptides interfered with the adhering of the proteins to DNA. Therefore, shorter (KW)$_2$KKA peptides were linked to both termini of the fluorescent protein, thereby preparing fluorescent proteins having a structure of (KW)$_2$KKA-eGFP-AKK(WK)$_2$. The use of the fluorescent protein having a structure of (KW)$_2$KKA-eGFP-AKK(WK)$_2$ could clearly stain DNA without noise, thereby visualizing DNA (FIG. 1).

Analysis on Dissociation Constant of Fluorescent Proteins for DNA Staining

In order to analyze the dissociation constant of fluorescent proteins for DNA staining, electrophoretic mobility shift assay (EMSA) was conducted (FIG. 2). The dissociation constant, Kd, of the fluorescent protein for DNA staining, was determined to be about 14.7 μM, which is similar to 12.1 μM of EtBr, and higher than 12.1 nM of YOYO-1.

Analysis on DNA Sequence Specificity of DNA-Binding Peptide.

Figure 3A:
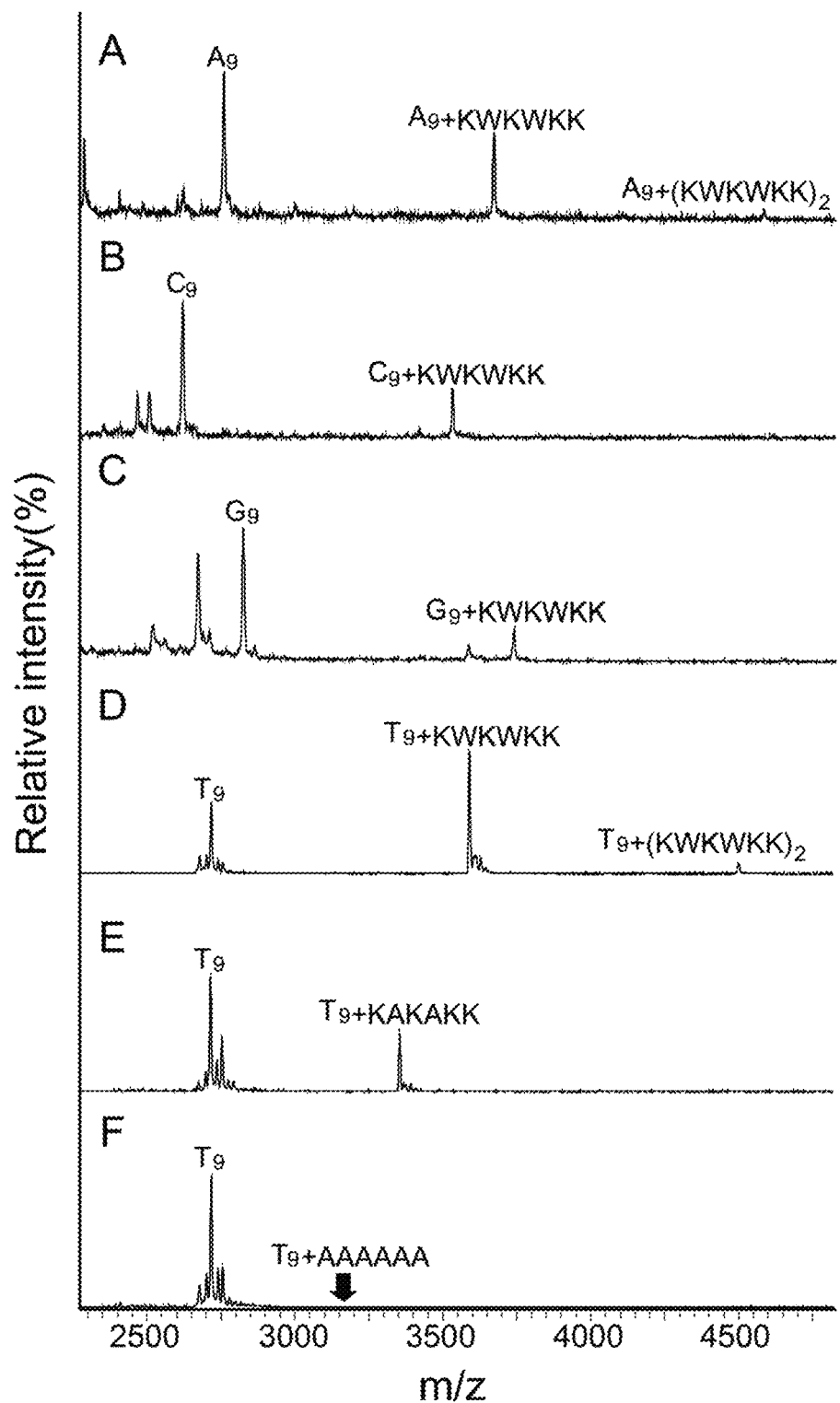
FIG. 3a shows binding affinity with A, C, G, and T and tryptophan effects through MALDI-TOF mass spectrometry.

It was found that the staining of single DNA molecules was not entirely uniform (FIG. 1), which indicates that the DNA molecules are likely to be stained in a sequence-specific manner. According to existing study results, KWK$_n$ peptides have been reported to exhibit a binding preference in the order of thymine (T), adenine (A), and cytosine (C) (7, 8). Therefore, it can be inferred that KWK peptides have higher affinity to AT-rich sequences, and MALDI-TOF mass spectroscopy was conducted in order to investigate the above inference. As a result, the preference matching expectations could be confirmed (FIG. 3*a*). The peptides composed of lysine and tryptophan were analyzed by the binding with oligonucleotides composed of A$_9$ (A), C$_9$ (B), G$_9$ (C), and T$_9$ (D). Through the comparison of relative intensity, the peptides are strongly bound to A and D (that is, DNA molecules having adenine and thymine). E, as a control, represents a peptide having alanine substituted for tryptophan, and it could be confirmed that E shows lower relative binding affinity than D. F, as a control, represents a peptide having the entire sequence composed of alanine residues, and it could be seen that F did not bind to DNA. It could be seen from the above results that the peptides including lysine and tryptophan residues had high affinity to DNA and the highest affinity to T in DNA nucleotide sequence.

Figure 3B:
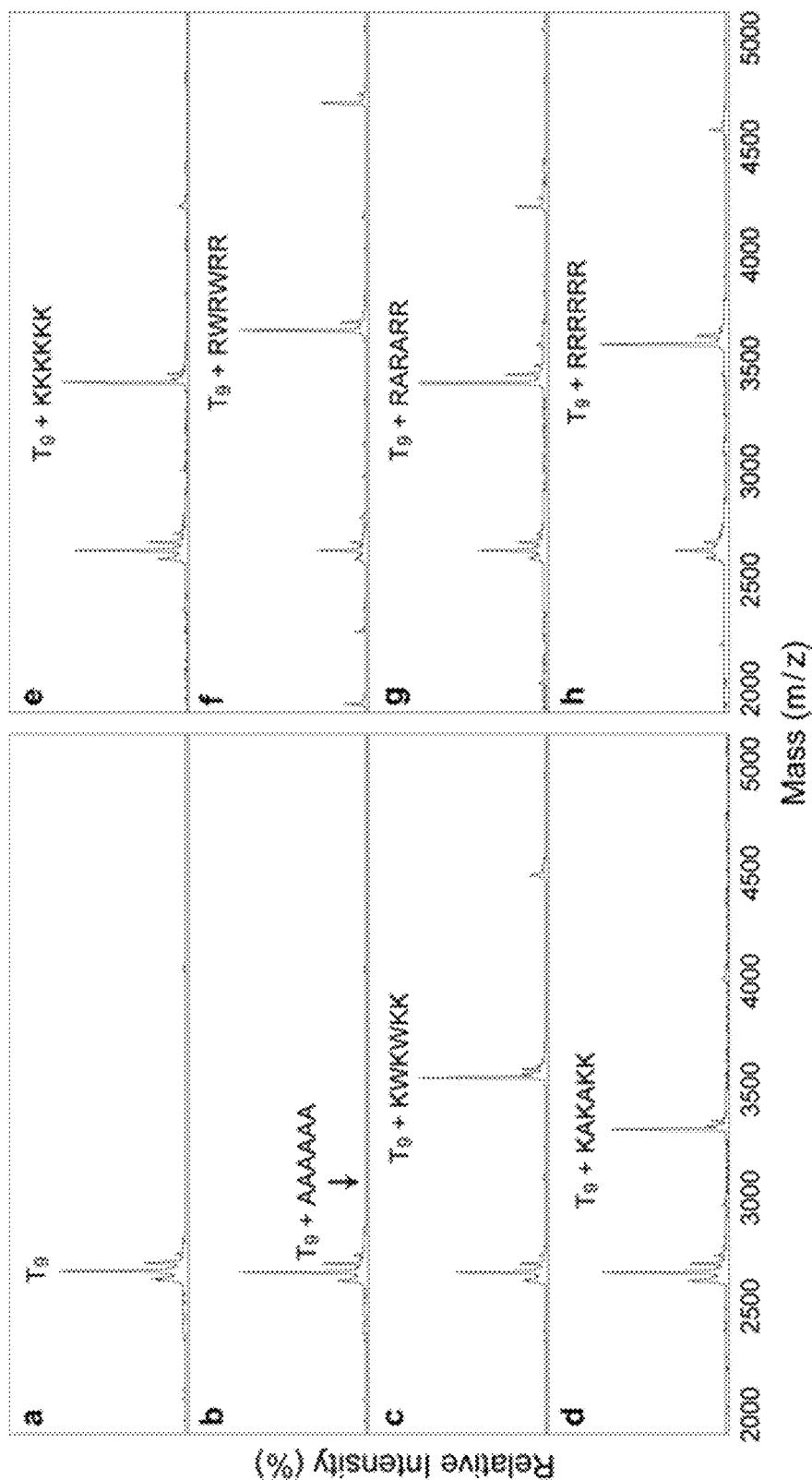
FIG. 3b shows binding affinity when lysine was substituted with arginine, through MALDI-TOF mass spectrometry.

Meanwhile, it was investigated whether DNA-binding peptides have binding strength when the lysine residue is substituted with another positively charged amino acid residue. MALDI-TOF mass spectroscopy was conducted with respect to the substitution of lysine with arginine (Arg, R) (FIG. 3*b*). As a result of analyzing oligonucleotides composed of T9 bound to RWRWRR and RRRRRR, the oligonucleotides were confirmed to have the same binding affinity as KWKWKK or KKKKKK. These results show that, for the binding peptides of fluorescent proteins for DNA staining of the present invention, arginine may be used instead of lysine.

In Vivo DNA Staining Using Fluorescent Proteins for DNA Staining

Figure 4:
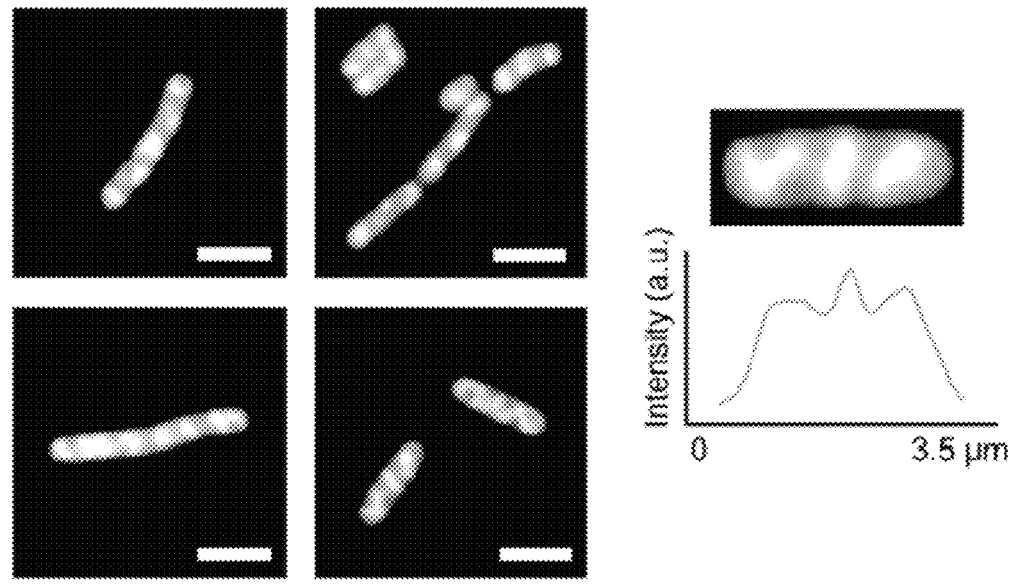
FIG. 4 illustrates images showing DNA staining by DNA staining fluorescent proteins in *E. coli* (BL21) cells. Panel (a) illustrates images showing *E. coli* (BL21) cells expressing eGFP-KWKWKKA peptide and a diagram showing fluorescent signal intensity corresponding thereto; and Panel (b) illustrates images showing *E. coli* cells expressing eGFP without the peptide as a control and its fluorescent intensity. Scale bars are 5 μm.
Figure 4:
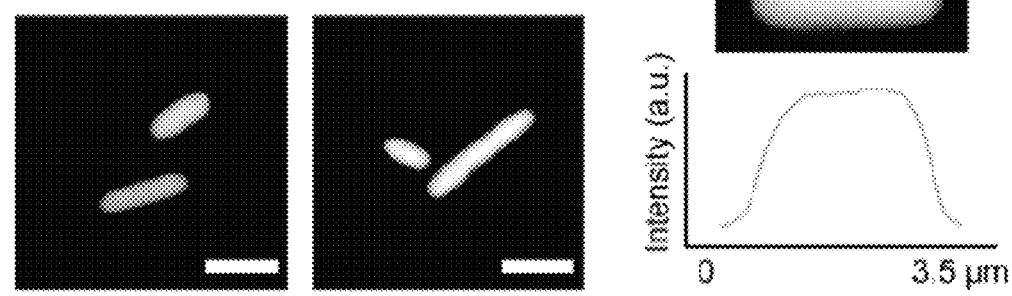

In order to investigate whether DNA molecules are in vivo stained using fluorescent proteins for DNA staining, the test was conducted in bacterial cells (*E. coli*, BL21) using (KW)$_2$KKA-eGFP-AKK(WK)$_2$ as fluorescent proteins. In comparison with general eGFP used as a control, fluorescent proteins for DNA staining showed distinct patterns in growing cells (FIG. 4). Fluorescent proteins for DNA staining were localized in three or four discrete regions, such as both ends and the middle point of the bacterial cells. These results are in concordance with existing bacterial DNA images obtained by visualizing bacterial DNA using DNA polymerase linked to green fluorescent proteins, and thus these results indicate that the fluorescent proteins for DNA staining of the present invention can successfully stain DNA in vivo.

Analysis on Photocleavage by Fluorescent Proteins for DNA Staining

Figure 5:
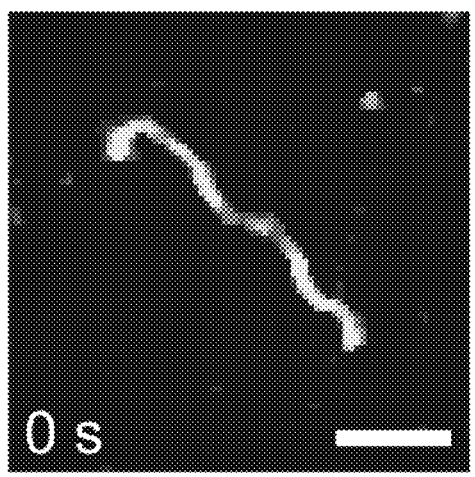
FIG. 5 illustrates images showing the suppression of photocleavage when DNA staining fluorescent proteins were used. Scale bars are 5 μm.
Figure 5:
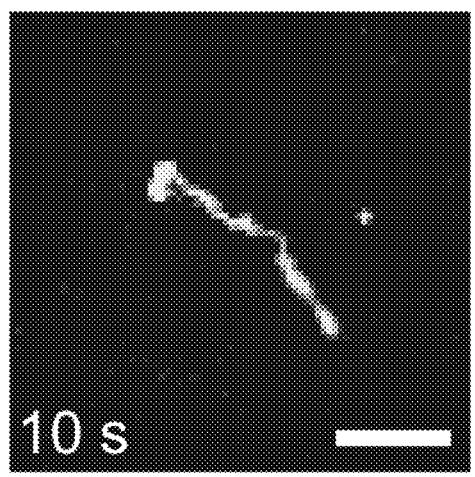
Figure 5:
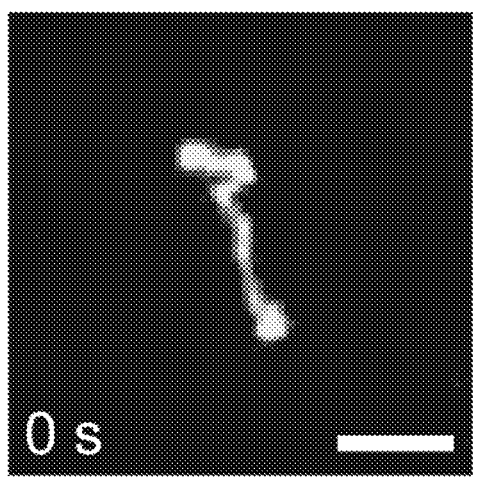
Figure 5:
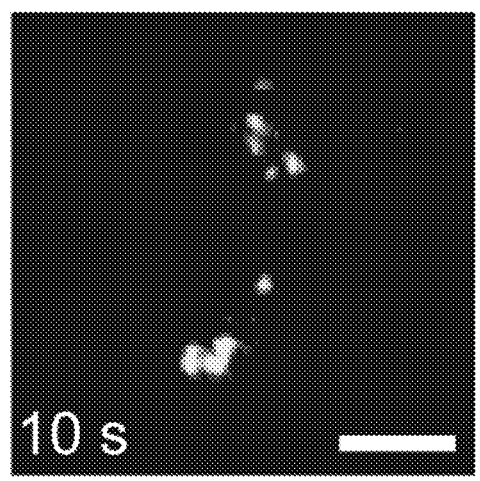

In order to investigate whether fluorescent proteins for DNA staining cause photocleavage, like in the existing DNA staining materials, DNA molecules stained with fluorescent proteins for DNA staining were exposed to a laser for 10 seconds, followed by observation. As a result of observation, the DNA molecules stained with fluorescent proteins for DNA staining were not damaged, but DNA molecules stained with YOYO-1 were completely broken (FIG. 5). In general, DNA staining organic dyes easily induce DNA cleavage through a laser, and the reason is that the fluorescent is highly likely to increase the possibility of causing a photochemical reaction in the vicinity of DNA frames while passing through numerous excitation-emission procedures. However, the fluorescent proteins for DNA staining of the present invention has a reduced risk of photocleavage since a portion binding to DNA (peptide) and a fluorescent portion (eGFP) are spatially separated. The fluorescent proteins for DNA staining of the present invention has a reduced risk of photocleavage as described above, thereby allowing imaging for a long period of time, which cannot be achieved by the existing DNA staining materials.

Reversible Staining

Figure 6:
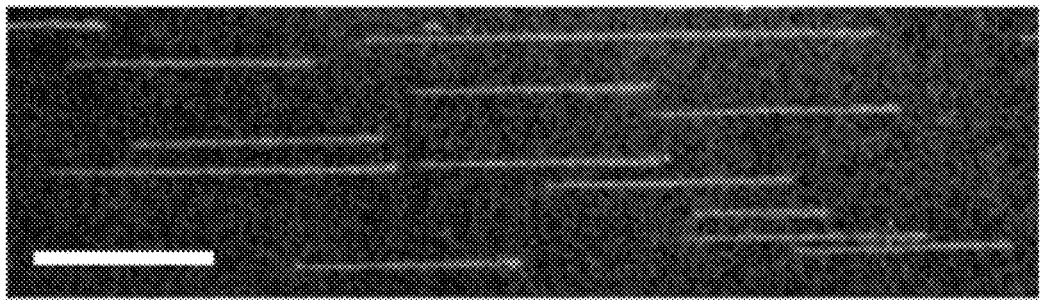
FIG. 6 illustrates images showing reversible staining when DNA staining fluorescent proteins were used. The biotin-labeled λ DNA was attached to a surface modified with Neutravidin, and the reversible staining of DNA is allowed by the pH of buffers in a flow channel. Scale bars are 10 μm.
Figure 6:
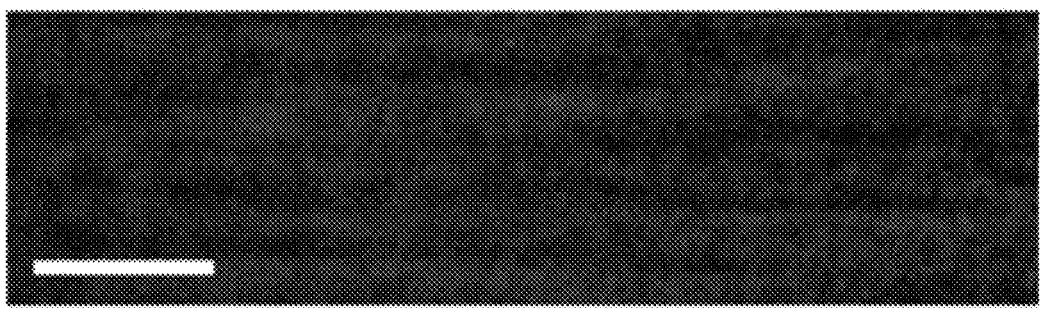
Figure 6:
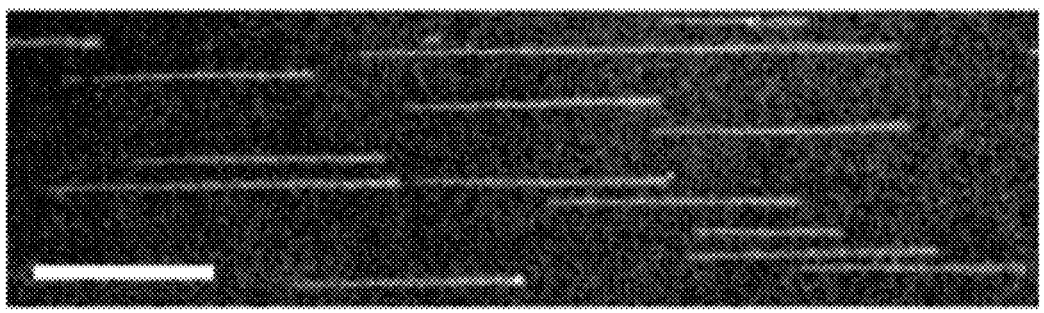

The possibility of reversible staining was investigated using fluorescent proteins for DNA staining. For this, the change in DNA staining state was investigated while the pH value was changed by stages (FIG. 6). As a result of observation, at an initial condition, pH 8, DNA molecules visualized by the fluorescent proteins for DNA staining were changed to be dark by flowing a buffer of pH 11, but thereafter, when the fluorescent proteins for DNA staining, which were dissolved in a buffer of pH 8, are allowed to flow into a flow cell, DNA molecules were confirmed to be stained again. This staining-decolorizing circulation showed the same result in spite of several repetitions. These results indicate that, when the fluorescent proteins for DNA staining of the present invention are used, reversible staining is allowed through only a simple procedure, such as adjusting pH. Therefore, the exchange of the observation-ended fluorescent proteins with novel fluorescent proteins using the above features may be a large benefit in tests requiring continuous tracking and observation.

Figure 7:
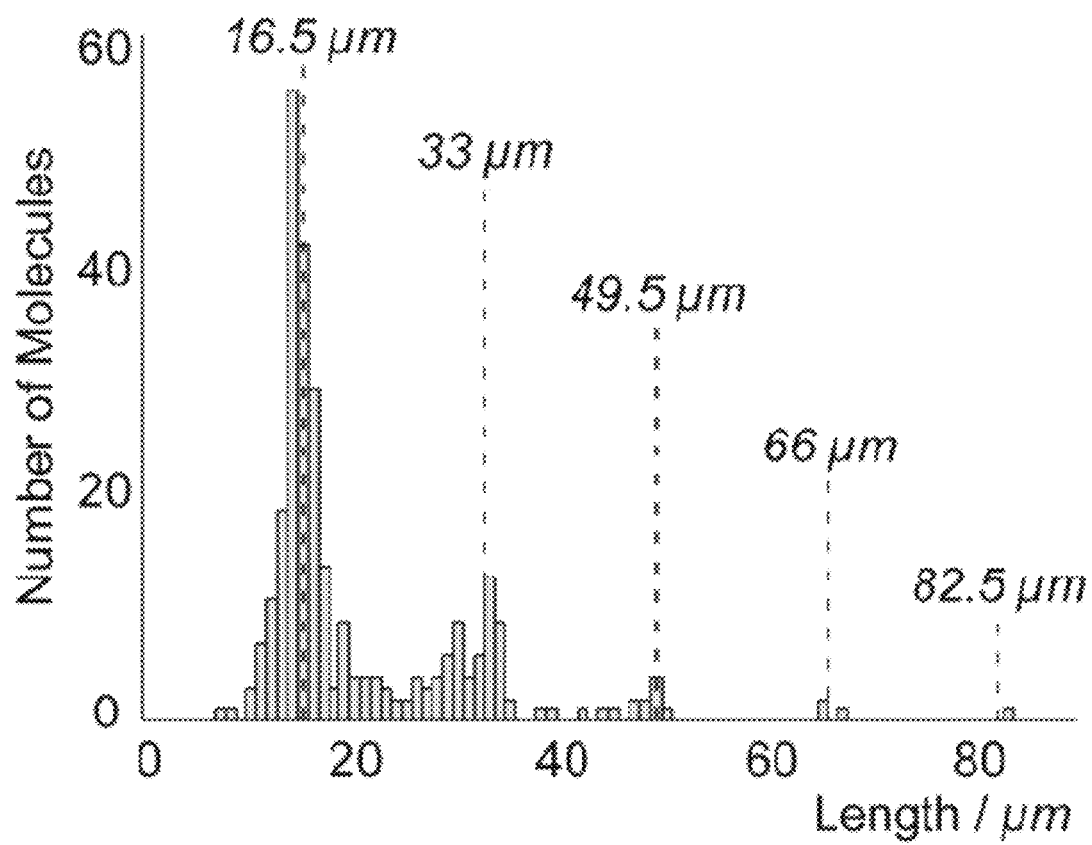
FIG. 7 illustrates a drawing showing the same contour length even with the use of DNA staining fluorescent proteins. The histograms of contour lengths of stretched λ DNA and its concatemers matches the theoretical contour lengths of λ concatemers (48,502 bp×0.34 nm/bp=16.49 μm), as represented by the dotted lines.

Analysis on Influence on DNA Contour Lengths by Fluorescent Proteins for DNA Staining In order to investigate whether DNA contour lengths are changed by fluorescent proteins for DNA staining, the full contour length of λ DNA, of which one end was fixed, was observed using a microfluidic flow cell (FIG. 7). As a result of observation, the λ DNA monomers were determined to be about 16.5 μm long, which matches the theoretically expectable value of 16.49 μm (48,502 bp×0.34 nm/bp=16.49 μm). These results indicate that the fluorescent proteins for DNA staining do not influence the contour lengths, unlike the staining with YOYO-1 or the like. It is estimated that the indole ring of tryptophan was partially inserted into stacked bases so that the insertion of tryptophan does not influence DNA contour lengths.

The invention has been described in detail with reference to preferred embodiments thereof. However, it will be appreciated by those skilled in the art that the specific technical features are merely preferred embodiments of the present invention and they should not be construed as limiting the scope of the present invention, and thus the substantial scope of the present invention shall be defined in the appended claims and their equivalents.

REFERENCES

[1] A. N. Glazer, H. S. Rye, Nature (1992) 359, 859-861.
[2] R. P. Haugland, S. T. Yue, P. J. Millard, B. L. Roth, Google Patents, 1995.
[3] M. A. Tycon, C. F. Dial, K. Faison, W. Melvin, C. J. Fecko, Analytical Biochemistry (2012) 426, 13-21.
[4] Y. Kim, K. Jo, Chem Commun (2011) 47, 6248-6250.
[5] Montenay. T, C. Helene, Nature (1968) 217, 844-&; C. Helene, J. L. Dimicoli, FEBS Lett (1972) 26, 6-10.
[6] J. L. Dimicoli, C. Helene, Biochemistry (1974) 13, 714-723.
[7] D. P. Mascotti, T. M. Lohman, Biochemistry (1992) 31, 8932-8946.
[8] D. P. Mascotti, T. M. Lohman, Biochemistry (1993) 32, 10568-10579.

What is claimed is:

1. A composition for DNA staining, the composition being represented by General Formula 3 and containing a DNA-binding peptide and a signal-generating material:

$$(XY)_m\text{-(signal-generating material)-}(X'Y')_n \quad \text{General Formula 3}$$

wherein in the above general formula, X is Lys or Arg, Y is Trp or Tyr, and the order of X and Y may be inverted; X' is Lys or Arg, Y' is Trp or Tyr, and the order of X' and Y' may be inverted; m and n each are an integer of 1 to 10; and (XY) and (X'Y') are indirectly linked to the signal-generating material via a linker,
wherein when XY is inverted, X'Y' is not inverted, and
wherein when X'Y' is inverted, XY is not inverted.

2. The composition of claim 1, wherein the linker is a peptide linker including at least two amino acids selected from the group consisting of glycine, serine, lysine, and alanine.

3. The composition of claim 2, wherein the linker is a peptide linker including glycine and serine.

4. The composition of claim 2, wherein the linker is a peptide linker including lysine and alanine.

5. The composition of claim 1, wherein m and n each are an integer of 1 to 5.

6. The composition of claim 1, wherein X and X' are Lys.

7. The composition of claim 1, wherein Y and Y' are Trp.

8. The composition of claim 1, wherein the signal-generating material is a fluorescent protein, a luminescent protein, a color reaction-catalyzing enzyme, a fluorescent material, a luminescent material, or a chemiluminescent material.

9. The composition of claim 8, wherein the signal-generating material is a fluorescent protein or a luminescent protein.

10. A method for staining DNA, the method comprising a step of applying the composition of claim 1 to a sample containing DNA.

* * * * *